(12) United States Patent
Lum et al.

(10) Patent No.: US 8,293,940 B2
(45) Date of Patent: Oct. 23, 2012

(54) PROCESS FOR RECOVERY AND PURIFICATION OF LACTIC ACID

(75) Inventors: Ooi Lin Lum, Singapore (SG); Govindharaju Venkidachalam, Singapore (SG); Yew Chin Neo, Singapore (SG)

(73) Assignee: Hyflux IP Resources Pte, Ltd., Singapore (SG)

( * ) Notice: Subject to any disclaimer, the term of this patent is extended or adjusted under 35 U.S.C. 154(b) by 591 days.

(21) Appl. No.: 12/443,413

(22) PCT Filed: Oct. 6, 2005

(86) PCT No.: PCT/SG2005/000341
§ 371 (c)(1),
(2), (4) Date: Jan. 12, 2010

(87) PCT Pub. No.: WO2007/040458
PCT Pub. Date: Apr. 12, 2007

(65) Prior Publication Data
US 2010/0145096 A1    Jun. 10, 2010

(51) Int. Cl.
*C07C 59/08* (2006.01)
(52) U.S. Cl. .......... 562/589; 562/580; 435/139
(58) Field of Classification Search .......... None
See application file for complete search history.

(56) References Cited

U.S. PATENT DOCUMENTS

| 6,433,163 | B1 * | 8/2002 | Ho .............. 540/315 |
| 6,509,179 | B1 | 1/2003 | Veldhuis-Stribos |
| 6,534,679 | B2 * | 3/2003 | Eyal et al. .......... 562/589 |
| 2004/0033573 | A1 | 2/2004 | Norddahl et al. |

FOREIGN PATENT DOCUMENTS
EP    265409 A    4/1988

* cited by examiner

*Primary Examiner* — Sudhakar Katakam
(74) *Attorney, Agent, or Firm* — Wells St. John P.S.

(57) ABSTRACT

The present invention relates to a process for recovery and purification of lactic acid from a fermentation broth containing lactic acid. The process comprises subjecting the fermentation broth to ultrafiltration and/or microfiltration to form a first permeate, concentrating the first permeate to form concentrated broth, subjecting the concentrated broth to supported liquid membrane for extraction of lactic acid into a separate stream, subjecting the extracted lactic acid solution to activated carbon for removal of color, subjecting the extracted lactic acid solution to cation exchange resin for demineriztion, subjecting the extracted lactic acid solution to anion exchange resin for removal of anionic impurities and concentrating the extracted lactic acid solution to desired concentration. The supported liquid membrane of the present invention contains an organic layer that comprises a earner, a co-extractant, a diluent and a stabilizer.

20 Claims, 2 Drawing Sheets

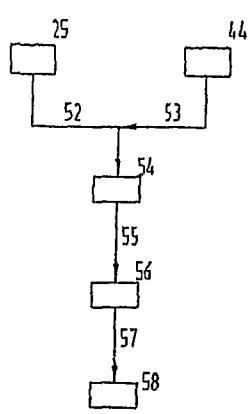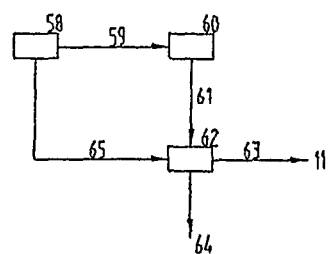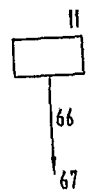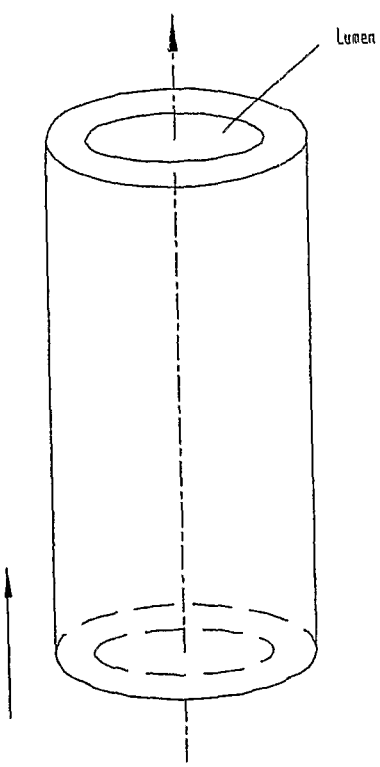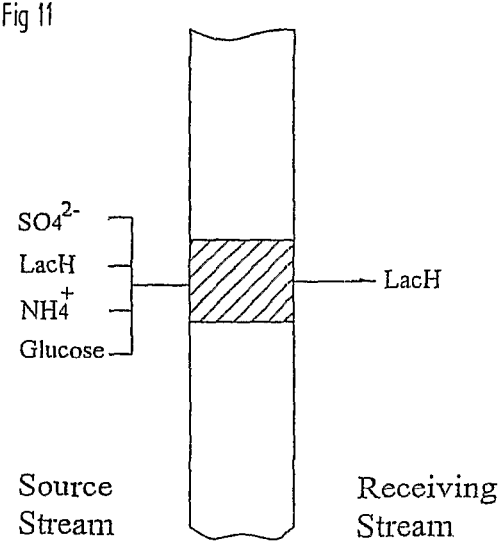

PROCESS FOR RECOVERY AND PURIFICATION OF LACTIC ACID

FIELD OF INVENTION

The invention relates to a process for the recovery and purification of organic acids, in particular, it relates to a process for the recovery and purification of lactic acid from fermentation broth containing lactic acid, using membrane technology.

BACKGROUND

The demand for organic acids, such as lactic acid, citric acid, ascorbic acid, gluconic acid or fumaric acid, has been increasing over the years, owing to their extensive use in food, pharmaceutical, detergent or biodegradable plastic industries. The fermentation processes achieve the production of organic acids at the industrial scale. Depending on the pH requirement of the bacteria strain used, the organic acids produced from the fermentation process is largely in salt form. The recovery of the organic acids from fermentation broth is a challenge to separation specialists.

Traditional process for recovery and purification of organic acids from fermentation broth generally involves one or several precipitation stage. For example, under the common industrial process for lactic acid production, the fermentation broth is generally heated to ca. 70° C. to kill the bacteria and then acidified with sulfuric acid to pH 1.8. The precipitated salt, which mainly constitutes of gypsum and biomass are removed by filtration and the resulting liquid is treated with activated charcoal to remove any coloring materials. The clarified liquid is then ion exchanged and concentrated to 80%. Smell and taste can be further improved by oxidative treatment, e.g., with hydrogen peroxide. The lactic acid obtained at this stage is usually of consumable quality but not suitable as pharmaceutical grade. Several additional purification steps are necessary to achieve that. The greatest disadvantage of the traditional process is the high loss of lactic acid during the crystallization steps.

Alternative downstream processing techniques have been researched for more environmental friendly downstream processing.

Several electrodialysis membrane technologies have been proposed as the key steps for recovery and purification of lactic acid. One possible way is to de-mineralized the lactic acid directly by using conventional electrodialysis membrane (i.e. cation & anion exchange membrane), where lactate salt (the broth, e.g. sodium lactate) is running in one stream, acid solution (e.g. hydrochloric acid) running in another, with two water streams running in between of the broth and the acid stream within the electrodialysis stack. The lactate passing through the anion exchange membrane combines with proton from the acid stream that passes through the cation exchange membrane to form lactic acid, while sodium chloride is formed in another water stream. This process produces sodium chloride as a side product.

To minimize chemical consumption and to achieve "zero" by-product, bi-polar electrodialysis membrane was proposed. Water splitting reaction occurs at the bipolar membrane, which generates the acidic proton for conversion of lactate to lactic acid and hydroxide ions for sodium cation to form sodium hydroxide. The sodium hydroxide solution is reusable by the fermentation step. Usually the clarified broths are purified and concentrated with conventional electrodialysis membrane first before subjected to bipolar electrodialysis stack.

The largest drawback of electrodialysis membrane is the requirement of high quality feed and the high operating cost associated with the high electric current necessary for fast organic acids transport, and the relatively high cost of the membrane, in particularly, the bipolar membrane. Besides, the selectivity may not always favor the desired outcome.

Another practical recovery technique is reactive liquid-liquid extraction, where the organic acids are being extracted into an organic phase with a suitable carrier. The organic acids are then back extract into aqueous phase. The carrier could be either cationic or neutral.

With neutral carrier, such as tertiary amine, the carrier will extract the organic acids directly, which means, protonation prior to extraction has to be carried out. The stripping aqueous phase can either be water alone or with chemical. The advantage of water stripping is clear. When the organic stripped is in its acid form with minimum impurities, the distribution ratio could be low. This will restrict the feasibility of direct water stripping. Other stripping agents such as sodium hydroxide, sodium chloride, hydrochloric acid etc., can also be used. These stripping agents have high stripping efficiency, but this would mean that there will be high "contaminants" (the stripping agent itself) present in the product and therefore, further purifications steps are necessary. An alternative method is to use a water-soluble tertiary amine as a back extractant. For example, trimethylamine (TMA) can completely back extract the organic acids from the organic phase. The organic acids are then recovered by decomposing the TMA-RCOOH complex at elevated temperature. The TMA is evaporated and collected for reuse, leaving the organic acids behind.

U.S. Pat. No. 6,472,559 B2, discloses the use of phase transfer extraction of lactic acid from aqueous phase to water insoluble amine rich organic phase under highly pressurized carbon dioxide environment. The lactic acid is back extract to aqueous phase after removal of carbon dioxide environment. The drawback of this technique is the use of large quantity of organic solvent.

With cationic carrier, usually in the form of quaternary amine, the carboxylate is exchanged with the counter ions of the amine and thus is extracted into the organic phase. The carboxylate is then stripped with salt or acid, which resulted in organic acid salt and organic acid, respectively, in the end stripping solution. Whichever way, large quantity of the stripping agents ("the contaminants") will be present in the stripping solution. Further purification steps need to be carried out to remove the contaminants.

Separation by liquid membranes has increasingly caught the attention of the researchers since the 1980s. There are few variants of liquid membranes, i.e., liquid emulsion membrane, hollow fiber supported liquid membrane, and flat sheet supported liquid membrane. Liquid membranes separate the organic acid through liquid-liquid partitioning of the source stream with an organic phase that contains an active carrier. The organic acid is being extracted into the organic phase and it is then being back extracted into aqueous phase through partitioning of the organic phase with the stripping solution. The "separation" mechanism of supported liquid membrane (SLM) is different from the normal membrane. The normal membrane separates components by size, whilst SLM extracts the interest component via chemical mean based on facilitated transport mechanism. The chemistry of SLM is basically liquid-liquid extraction. A significant advantage of SLM over liquid-liquid extraction is that it requires very minimum organic solvent, which result in friendlier operation.

However, the adoption of SLM in real industrial application has been limited by the stability (useful life) of the SLM that generally last only several hours. This is due to the lost of solvent and/or carrier to the aqueous phase. The Water that is being transported across the membrane layer plays an important role in destabilizing the membrane.

It is the object of at least one embodiment of the present invention to provide a complete downstream processing process for recovery and purification of organic acids, in particular, lactic acid from fermentation broth containing lactic acid using supported liquid membrane and other purification technologies.

SUMMARY OF INVENTION

The present invention is directed to a process for recovery and purification of lactic acid from a fermentation broth containing lactic acid. The process uses a supported liquid membrane that is suitable for the extraction of organic acid, in particular, lactic acid from the fermentation broth.

In one particular aspect, the invention is directed to a process for recovery and purification of lactic acid from a fermentation broth containing lactic acid, said process comprising:

a. subjecting the fermentation broth to ultrafiltration and/or microfiltration to form a first permeate;
b. concentrating the first permeate to form concentrated broth;
c. subjecting the concentrated broth to supported liquid membrane for extraction of lactic acid into a separate stream;
d. subjecting the extracted lactic acid solution to activated carbon for removal of colour;
e. subjecting the extracted lactic acid solution to cation exchange resin for demineration;
f. subjecting the extracted lactic acid solution to anion exchange resin for removal of anionic impurities;
g. concentrating the extracted lactic acid solution to desired concentration.

Preferably the supported liquid membrane comprises a base polymer and an organic layer impregnated on the pores of the base polymer.

Preferably the organic layer comprises a carrier, a co-extractant, a diluent and a stabilizer.

Preferably the stabilizer is a form, of ethoxylated fluorocarbon based surface-active agent that is non-ionic.

Preferably the stabilizer is selected from a group of ionic, non-ionic detergent or surfactant.

Preferably the carrier is selected from a group consisting of a primary, secondary and tertiary aliphatic and aromatic amine.

Preferably the co-extractant is an aliphatic alcohol.

Preferably the diluent is selected from a group consisting of hydrocarbon, ketone, ether and ester.

Preferably the amine has an alkyl chain of $C_6$ to $C_{24}$.

Preferably the amine has branched, linear or cyclic side chains.

Preferably the aliphatic alcohol has carbon chain of $C_2$-$C_{29}$.

Preferably the carbon chain can be linear or branched.

Preferably the base polymer is constructed from a group consisting of polypropylene, polyethylene, polyvinyldifluoride, polyethersulfone, polysulfone and polyvinylsulfite.

Preferably the base polymer is constructed from ceramic and metallic materials.

Preferably the supporting liquid membrane is of a hollow fiber configuration comprises two sides, one side is of an organic phase and the other side is of an aqueous phase.

Preferably the organic phase contains at least two or more components.

Preferably the ultrafiltration is carried out using ultrafiltration membrane of pore sizes from 0.1 to 0.01 µm.

Preferably the microfiltration is carried out using microfiltration membrane of pore sizes from 0.04 to 1

Preferably the concentrated broth has a pH value of from 1 to 4.8.

Preferably the process further comprises the step of feeding into the supported liquid membrane in step (c) with water or water mixed with solutes.

Preferably the process further comprises a step of subjecting the solution obtained from step (f) to activated carbon process.

BRIEF DESCRIPTION OF DRAWINGS

The present invention will be further explained with reference to the appended figures, wherein:

FIG. 7 illustrates the polishing stage.

FIG. 8 illustrates the product evaporation stage (with optional polishing stage).

FIG. 9 illustrates the water reclamation stage.

FIG. 10 illustrates the flow design of supported liquid membrane.

FIG. 11 illustrates the extraction process of supported liquid membrane.

DETAILED DESCRIPTION OF THE INVENTION

The present invention is directed to a process for recovery and purification of organic acids, in particular, lactic acid, from fermentation broth containing lactic acid. The process described herein can accept lactic acid fermentation broth with any concentration from 1% lactate or higher, in particular, 8% or higher.

The first step of the present invention involves a membrane, filtration technique for separating main bulk of impurities present in the fermentation broth, such as biomasses. This produces a clarified broth that is much clearer and almost free of suspended solids. This separation is carried out with ultrafiltration (UF) and/or microfiltration (MF) membrane technology.

Figure 1:
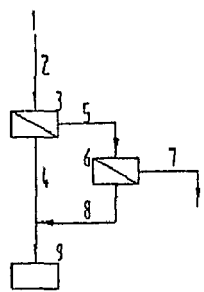
FIG. 1 illustrates the filtration process for raw fermentation broth.

In accordance with FIG. 1, a fermentation broth containing lactic acid 1 is first fed into apparatus 3 via line 2. The apparatus 3 is an ultrafiltration (UF) membrane. The UF membrane has filtration pore sizes of 0.1 to 0.01 µm. The UF membrane can be in several configurations such as hollow fiber, tubular, flat sheet or spiral wound unit. In the preferred form, hollow fiber membrane is used which provides the best surface area to volume ratio against other configurations. The UF membrane of the present invention can be made of polymeric, ceramic or metallic materials. The UF membrane acts as a form of barrier that blocks the suspended solids, biomass, bacteria, but not limited thereto.

The filtration method engages in the UF membrane can either be a cross-flow method or dead-end method. In the preferred form, cross-flow filtration is adopted. In cross-flow filtration, the process stream flows parallel to the membrane rather than perpendicular to it as in the case of the deed-end method. Only a portion of fermentation broth passes through the membrane as compared to the dead-end filtration method. The flow of fermentation broth parallel to the membrane is of sufficient velocity to wash the retained particulates away from the surface. This continual sweeping action minimizes the build up of the particulates on the surface of the membrane and hence, extending the filtration cycle.

In the cross-flow method, the ultrafiltration membrane can achieve recovery of about 30 to 99%, in particular, 60 to 95% of the fermentation broth.

For higher recovery of the fermentation broth, concentrate from apparatus 3 is passed through line 5 into apparatus 6, a microfiltration (MF) membrane where remaining particulates and/or precipitates in the concentrate can be removed. The MF membrane has pore sizes of 0.1 to 1 μm. The MF membrane can achieve about 50 to 90% recovery of the fermentation broth, which increases the recovery of membrane filtrate (both UF and MF) to about 90 to 99%.

Both MF & UF are low-pressure membrane processes used to separate bacteria, viruses (UF only), and high molecular weight compounds colloidal and particulate matters from a feed stream. Both have larger pores and high permeability with less osmotic effects that allow them to operate at relatively low pressure than nanofiltration (NF) and reverse osmosis (RO) and are least costly to operate. As a result, they require fewer membrane elements and lower pressure for operation. Since the separation is based on size, they are useful for the separation of delicate materials since it is a non-denaturing method of separation. In general, salts and low molecular weight species can pass through the membrane while suspended solids become concentrated on the other side of the membrane.

Further recovery of the lactic acid is achieved by microfiltration (MF) of lactic acid fermentation broth with addition of water into the feed. This process is called diafiltration. Combination of MF and diafiltration is used for higher recovery of lactic acid. The MF membrane can be in several configurations such as hollow fiber, tubular, flat sheet or spiral wound unit. It can be made of polymeric, ceramic or metallic materials.

In another embodiment, combined MF-diafiltration can be adopted to purify the fermentation broth directly to achieve more than 99% recovery of the lactic acid without subjecting the fermentation broth to ultrafiltration.

In the present invention, lactic acid can be recovered from the clarified broth obtained after UF and/or MF. In a situation where the fermentation broth 1 has low initial lactate concentration, in particular, 25% or lower, the clarified broth obtained thereto has to be concentrated to improve the recovery/extraction rate. The present invention utilizes suitable sized evaporator 9 to concentrate the clarified broth to higher concentration, in particular, 20 to 60% of lactate in the clarified broth, and yet in particular, at a concentration of 30 to 55%.

Figure 2:
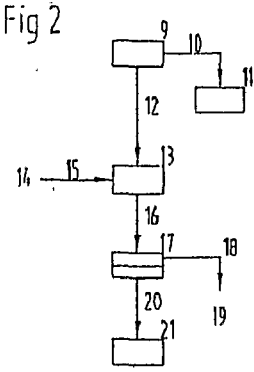
FIG. 2 illustrates the main process fluid concentration stage.

The distillate obtained after evaporation process contains less than 0.5% of lactate. In present invention, the distillate is practically water with some volatile organic carbons (VOCs) and lactic acid. It is easily clarified by passing through an activated carbon column (apparatus 11 as shown in FIG. 2) via line 10 to generate grade one quality water 67. Alternatively, the distillate can be reused in the fermentation broth for preparation of fermentation medium.

In situation where the fermentation broth's initial pH is higher than its pKa (Lactic acid pKa=3.86), the concentrated clarified broth would require pre-acidification before the extraction process begins. The acidification agent 14 (as shown in FIG. 2) suitable for use in the present invention is inorganic acid such as hydrochloric acid or sulfuric acid. In the preferred form, sulfuric acid is used as it does not carry much fume and moisture and thus would not cause much reduction in lactate concentration. The objective of acidification is to convert lactate salt in fermentation broth to lactic acid. In general, pH is the controlling factor for the adjustment. Fermentation broth usually has pH of 5 to 6.5, and should be adjusted to lower than the pKa of the organic acid, in particular 1.5 to 3.8 for lactic acid broth, and yet more preferably 2 to 3.6 for lactic acid broth. If the fermentation broth already reached a low pH; no further acidification is required. The amount of acidification agent 14 required is dependent on the initial pH of the fermentation broth.

Upon cooling of the fermentation broth in tank 13, inorganic salt 19 may precipitate out of the solution. The inorganic salt 19 formed thereto is dependent on the base and the acidification agent 14 used to control the fermentation pH during fermentation. For example, if ammonium hydroxide is used for controlling fermentation pH and sulfuric acid is used for the acidification, the inorganic salt 19 formed thereto would be ammonium sulfate. Another reason that sulfuric acid is a preferred acidification agent is that sulfate salt generally precipitates easily as compared to other acidification agents.

Acidification of Ammonium Lactate to Lactic Acid with Sulfuric Acid

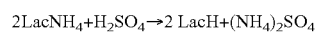

$$2LacNH_4+H_2SO_4 \rightarrow 2\ LacH+(NH_4)_2SO_4 \qquad \text{Equation 1:}$$

The acidification process is exothermic and thus it regenerates heat and resulting in an increase of solution temperature. After the solution is cooled to approximately 50° C., ammonium sulfate will start to precipitate out. A vast quantity of sulfate will crystallize out when the solution is cooled to room temperature (25° C.). In fermentation, lactate salt can be calcium lactate, sodium lactate or ammonium lactate. During acidification using sulfuric acid, corresponding sulfate salt will be produced.

If any salt is formed during the process, they will be filtered off. In general, salt forms a substantial quantity if (i) the initial fermentation broth has a pH of 5 or higher (in sodium or ammonium lactate); (ii) sulfuric acid is used as the acidification agent; and (iii) the concentration of the fermentation broth has been increased to more than 20% during evaporation stage. The separation of the fermentation broth with the salt is effected through apparatus 17. Apparatus 17 can be filter press or any other solid-liquid separators.

The filtered acidified broth generally contains minimum suspended solids. Depending on the concentration, the filtered acidified broth can be a clear solution or dark viscous liquid containing more than 20% of lactic acid, in particularly 20 to 48% of lactic acid.

Figure 3:
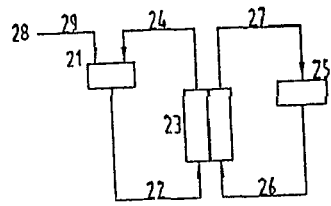
FIG. 3 illustrates the main supported liquid membrane stage.
Figure 4:
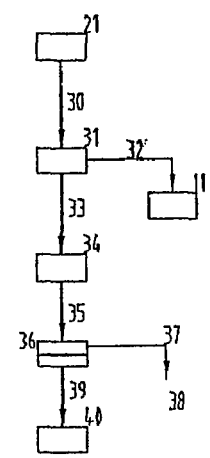
FIG. 4 illustrates the supporting process fluid concentration stage.
Figure 5:
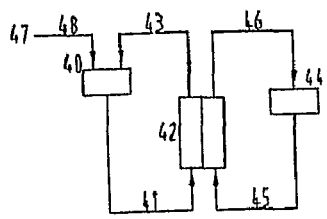
FIG. 5 illustrates the supporting supported liquid membrane stage.
Figure 6:
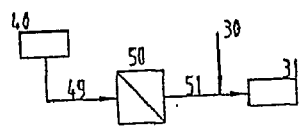
FIG. 6 illustrates the supporting ultrafiltration stage.

Recovery of lactic acid takes place when the filtered acidified broth is fed into an apparatus 23 as shown in FIG. 3. The apparatus 23 that is used for the extraction of lactic acid is known as supported liquid membrane (SLM).

The membrane layer of the SLM is an organic layer that consists of suitable components that are impregnated on another membrane (base membrane), such as ultrafiltration (UF) or microfiltration (MF) type membrane. In the preferred form, MF membrane is used due to its higher pore area density. The base membrane used in SLM has hydrophobic nature and is made from hydrophobic polymer, such as polypropylene (PP), polyvinyldifluoride (PVDF) and polyethylene (PE); amphoteric polymer such as polysulfone (PSF), polyethersulfone (PES) and polyvinylsulfite (PVS). Hydrophobic polymer is the more preferred base membrane material; In the most preferred form, PP polymer is used, owing to its highly hydrophobic nature, relatively low cost, good mechanical properties and good chemical stability.

In the SLM of the present invention, the organic layer that is impregnated into the base polymer stabilizes the impregnated layer within the containment of micro pores of the membrane during rugged operations. The said organic layer contains four components: carrier, co-extractant, diluents and stabilizer.

The carrier comprises a water insoluble amine, in particular, primary, secondary or tertiary aliphatic amine. More preferably, it comprises an amine with an alkyl chain of $C_4$ to $C_{24}$. In the most preferred form the carrier is a tertiary aliphatic amine with alkyl chain of $C_8$-$C_{12}$.

The co-extractant is a liquid that assists the carrier in the extraction process. In the preferred form, the co-extractant is an aliphatic alcohol that has minimum or no water miscibility, in particular, it is an alcohol with carbon chain of $C_4$-$C_{18}$ and more particularly, it is an alcohol with carbon chain of $C_6$-$C_{10}$. The alcohol functionality can be at the end of the carbon chain (normal alcohol) or at the branch. In the most preferred form, the co-extractant is either normal chain alcohol with $C_8$-$C_{10}$ or branch chain alcohol with $C_6$-$C_9$.

A diluent is added to the organic layer to dilute the concentration of the carrier so as to increase the viscosity of the carrier to aid in the extraction rate. In generally, any organic liquid that is compatible to the base membrane and not water miscible can be used. Suitable diluents include hydrocarbon, ketone, ether, or ester. In particular, kerosene, methyl isobutyl ketone, mono-isobutyl ketone and butyl acetate are the more preferred diluents, and yet the most preferred diluent is kerosene, which is relatively cheap.

The stabilizer is a component that helps to stabilize the organic components, i.e., extractant, co-extractant and diluent in the base membrane. The useful life of a SLM is dependent on the rate at which the organic components loss to its surrounding, i.e., the aqueous phase. In common SLM, this occurs within few hours. Toshio Shinbo et al. has reported [Journal of Membrane Science, 84 (1993) 241-248] that the main reason of instability of SLM is the solubility of the organic phase in the aqueous phase. In their report, SLM with chiral crown ether (carrier) and solvent was used for enantioselective separation of amino acid. The system with more water-soluble solvent, i.e., o-Nitrophenylphenyl ether and 2-fluoro-2'-nitrodiphenyl ether shows very poor membrane stabilities. Their result indicates that the membrane start to loss their stabilities within first day of operation. When less water-soluble solvent, i.e., o-Nitrophenyl octyl ether and p-Nitrophenyl heptyl ether were used, the membrane is stable up to approximately 50 days. The poorer stability of the "more" water-soluble solvent system was improved by pre-heating the aqueous solution in its solvent. Practically, the addition of solvent into the process liquid is undesirable as it adds on organic impurities into the process liquid. The stabilizer improves the stability of the SLM without the addition of organic solvent into the process liquid.

In the present invention, the stabilizer is a non-ionic surface-active agent that has very low solubility in water. The surface-active agent has low aqueous surface tension. The stabilizer while in the organic composition, acts as a barrel between the organic and the aqueous phase and therefore reduces the mixing of the two phases. Three primary groups of stabilizer are suitable for USG in the present invention and they are: hydrocarbon based, silicone based and fluorocarbon based stabilizer. The non-ionic surfactant is fluorocarbon based. Non-ionic surfactant is a form of surface-active agents without ionic head group. The hydrophilic group of the fluorocarbon based surfactant is non-ionic ethoxylated group and hence with very minimum water solubility. The tail group of the fluorocarbon based surfactant is both hydrophobic and lipophilic. This ensures that the stabilizer will predominantly resident at solvent-aqueous interface. The boundary creates by the fluorocarbon based surfactant minimizes the mixing of water with the organic solution in the membrane and thus minimizes water transport across the membrane and therefore prolong the stability of the SLM membrane. The non-ionic nature of the surface-active agent also acts as an additional barrier to the ionic species and thus improves the selectivity of the membrane towards organic acid. Comparatively, the organic acid in its acid form is less resisted by the surfactant, while inorganic acid such as sulfuric acid and hydrochloric acid are fully ionized in aqueous medium and thus is restricted for entering the liquid membrane phase (since water transport is limited). This results in a much better selectivity between organic acid and inorganic acid. In a typical experimental setup with liquid membrane composition of 0.01% stabilizer, the selectivity could be as high as few thousands times. Similarly, the restriction of water-liquid membrane interaction also minimizes the transport of glucose across the membrane. The SLM of the present invention which comprises a suitable selection of the extractant, co-extractant and diluents mentioned above is stable for more than 180 days. In general, stabilizer in an amount of from 0.001 to 10% can be added. Higher amount of the stabilizer gives rise to a more stable membrane but with lower extraction rate. The most preferred stabilizer concentration is from 0.005 to 0.020 ppm. The fluorocarbon based non-ionic surfactant has a general structure of $R_fCH_2CH_2O(CH_2CH_2O)_xH$, where x is a number ranges from 0-25, and $R_f$ is fluorocarbon group $F(CF_2CF_2)_y$, where y is 1 to 20.

The carrier, co-extractant, diluent and stabilizer are mixed into a homogeneous phase before impregnated into the pores of the base membrane. The base membrane is preferably in hollow fiber configuration. The apparatus 23 permits the flow of one stream along the lumen of the fibers while another stream along the shell side of the fibers. A more preferred arrangement is to let the source solution, i.e. the fermentation broth, to run along the shell side while the receiving solution (refer to as stripping solution) along the lumen. Both solutions are re-circulating along the respective side: source solution along line 22 (as shown in FIG. 3) into apparatus 23 and along line 24 to bring the solution back to tank 21; the receiving solution transfer along line 26 into apparatus 23 and along line 27 to bring the solution back to the holding tank 25. The pH of the source phase is being maintained at lower than the pKa, and specifically 1.5 to 3.6 for lactic acid solution by acid 28 via dosing line 29. Acid 28 is generally the same as the acidification agent 14. The receiving solution could be water alone, or contains chemical such as hydrochloric acid or sodium carbonate. The most preferred receiving solution is plain water, as this would minimize the polishing effect in later stage. The extraction processes involve three steps:

(I) Protonation of Carrier with Organic Acid

During the protonation, the organic acid is being attached to the amine (II) Transfer of Lactic Acid Across the Organic Layer to the Receiving Solution Side The amine-lactic acid complex is transporting across the organic layer from source solution side to receiving solution side. The transportation mechanism is either diffusion of the complex or hoping of the lactate molecules:

$$[R_3NH^+Lac]_{org}+[R_3N'] \leftrightarrow [R_3N'H^+Lac^-]_{org}+[R_3N]$$

where N' is closer to the receiving end, and at the receiving end, (III) Deprotonation of Amine $$[R_3N'H^+Lac^-]_{org} \leftrightarrow [R_3N']_{org}+[LacH]_{aq}$$

the lactic acid (or organic acid in general) is transfer from source solution to the receiving solution.

The ratio of the quantity of source to receiving solution is preferably from 1:1 to 8:1, and yet more preferably, from 1:1 to 4:1. The extraction process time is depending on the source to receiving ratio, organic acid concentration, and extraction apparatus (i.e. the supported liquid membrane). In realistic, the extraction process should be stopped when source phase organic concentration is not more than 20% higher than the receiving phase, since the extraction rate would be too slow. The receiving solution would be collected for further treatment. A fresh receiving phase is circulated in the system to further extract the lactic acid. After a few rounds of extraction, the source solution would contain less than 8% lactic acid, which would be less suitable for extraction as the extraction rate would become too slow. In a preferred embodiment where the source to receiving ratio is 2:1, and source phase lactic acid concentration is 48% initially; the source solution lactate concentration would reduce to 7 to 10% after six rounds of extractions of 3 to 5 hours each. The average lactic acid concentration in the receiving solution is 10 to 15%. The unique advantage of the apparatus 23 is the high selectivity of the membrane. In general, the receiving solution has no detectable glucose, which is the raw material for the fermentation of lactic acid. The color of the receiving phase is low relative to the source solution, since lactic acid is being extracted into a clean solution. Comparing with the clarified broth (after UF/MF), it could be 50 to 500 times reduction of color. The high selectivity nature of the SLM ensures that the receiving phase contains very minimum ionic impurities and practically independent of source phase ionic impurities concentration. In the execution of the preferred apparatus with initial source containing 48% lactate, a pH value of 3.2, 4.0 to 4.5% of ammonium, 10 to 20% of sulfate, the receiving solution would contain 0.0001 to 0.05% of ammonium and 0.0001 to 0.04% of sulfate.

To improve the recovery, the source solution is sent to another evaporator 31 via line 30 for concentration of the clarified broth up to 48% again. The capacity of the apparatus 31 is approximately 5 to 8 times smaller than apparatus 9. As the solution already contains ammonium sulfate at near saturation point, ammonium sulfate precipitates out during concentration.

The concentrated broth is being filtered in a similar manner as the previous process, via line 33 into a cooling tank 34 and out through line 35 into a filter press 36 to obtain a clear concentrated broth which is collected in tank 40 and ammonium sulfate crystal in 38. In this filtration step, no further pre-acidification is necessary as the concentrated broth is already at low pH. The clarified concentrated broth in tank 40 is then subjected to extraction of lactic acid with SLM of apparatus 42 using the same extraction method as described above for apparatus 23. The resulting broth solution is fed into apparatus 50 via line 49 for further ultrafiltration before directing the broth solution into apparatus 31 for further concentration.

All the receiving solutions from the SLM processes (collected in tanks 25 and 44) are combined to a stream that contains certain quantity of colouring compound that passed through the SLM. The combined stream is fed into activated carbon column apparatus 54 (as shown in FIG. 7) where reduction of the color of the solution takes place. The decolorized broth from apparatus 54 is then directed to a cation exchanger column apparatus 56 via line 55 for removal of any trace of cationic impurities. In general, any strong cation exchange resin can be used in apparatus 56. Use of macroporous type of the cation exchange resin is preferred. Besides removing the cationic impurities, the cation exchanger column 56 also further removes the color of the broth to an even lower value, which could be zero alpha depending on the initial color of the solution. The demineralized lactic acid solution is then further treated with an anion exchanger apparatus 58, where all anionic impurities are removed. A weak anionic exchange resin is required in apparatus 58. In the preferred form macroporous type resin is used.

The output from the anion exchanger apparatus 58 generally contains no color. In any process design where minimum color persists after an anion exchanger, the output from the anion exchanger is further subjected to colour removal in an apparatus 60 that contains polishing color removing resin or carbon.

The resultant solution generally contains 7 to 12% of lactic acid. If higher concentration of the resultant solution is required, then the solution can be subjected to further concentration with a product evaporator, i.e. apparatus 62 as shown in FIG. 8.

The distillate from apparatus 14, 28 and 62 can be treated with apparatus 11 to remove the volatile organic carbons (VOCs) and trace quantity of lactic acid to generate grade one quality water 67. The quantity of water 67 is generally sufficient to supplement 70 to 90% demand of the whole processes including washing of equipments.

Alternatively, the distillate from apparatus 14 and 28 could be used directly in the preparation of the fermentation broth, while the distillate from apparatus from 62 can be used as the receiving solution for the SLM.

The present invention is further illustrated by the following examples, which are not to be construed in any way as imposing limitations upon the scope thereof.

EXAMPLE 1

Ultrafiltration

253 L of fermentation broth was circulated in an ultrafiltration membrane system at feed pressure of 2 bar. The ultrafiltration membrane was polyethersulfone based hollow fiber membrane with an effective area of 3.5 m². The feed solution was fed and flowed in the lumen of the fiber. The reject pressure was controlled at 1.6 bar pressure. The trans membrane pressure was at 1.8 bar. The initial permeate flow rate was 1.9 L/min and decline to 0.5 L/min after 3 hours at 86% recovery. The average flux was 19.5 LMH. The suspended solid in the raw fermentation broth and the clarified broth was 3.88 g/L and 0.005 g/L respectively. The concentrate of the broth had suspended solid of 49.78 g/L.

| Parameters | Unit | Feed | Permeate | Concentrate |
|---|---|---|---|---|
| Volume | L | 253 | 220 | 16 |
| Suspended solid | g/L | 3.88 | 0.005 | 49.78 |
| Lactate concentration | g/L | 108.9 | 107.2 | 99.7 |
| Turbidity | NTU | 4580 | 1.2 | 52000 |

EXAMPLE 2

Microfiltration

Sixteen liters of concentrated broth of ultrafiltration (UF) (i.e. microfiltration (MF) feed) was circulated in stainless steel MF membrane with titanium dioxide coating. The membrane had pore size of 0.1 μm. The MF feed had 49.78 g/L of suspended solid. The MF was operated at 3 bar trans-membrane pressure. The average flux was 80 LMH

EXAMPLE 3

Concentration of Clarified Broth from 11% to 48%

100 L of clarified broth was concentrated from 11% to 48%. The quantity of the concentrated broth recovered was 22.9 L, while 77.1 L was collected as distillate.

| Parameters | Unit | Feed | Concentrate | Distillate |
|---|---|---|---|---|
| Volume | L | 100 | 22.9 | 77.1 |
| Lactate concentration | g/L | 100-105 | 475-485 | <0.2 |

EXAMPLE 4

Acidification and Crystallization of Ammonium Sulfate 77.2 L of broth containing 48.6% lactate was acidified from pH 5.6 to 3.2 with 13.8 kg of sulfuric acid. 6.1 kg (wet weight) of ammonium sulfate crystal precipitated out after acidification and the solution was cooled to 25° C. After filtering off the ammonium sulfate crystal, 82.2 L of the acidified broth was recovered. Lactate recovery was up to 99.5%.

| | Unit | Before acidify | After acidify and filter |
|---|---|---|---|
| Volume | L | 77.2 | 82.2 |
| pH | | 5.6 | 3.2 |
| Lactate concentration | g/L | 486.8 | 454.7 |
| Sulfate concentration | g/L | 16.8 | 186.5 |
| Ammonium concentration | g/L | 79.7 | 61.5 |
| Lactate quantity | kg | 37.58 | 37.38 |

EXAMPLE 5

Extraction of Lactic Acid with Supporting Liquid Membrane

The concentrated lactic acid broth with 40-48% lactate concentration was extracted with hollow fiber supported liquid membrane (SLM) with 70 m² membrane area. The organic layer impregnated to the membrane contained 0.001-10% carrier, 99.9-90.0% co-extractant and diluents. Water was used, as the receiving solution. The quantity of the receiving solution used was half the starting source solution volume per extraction that lasted 3 to 5 hours. The similar process was scaled up to industrial size module with effective membrane area of 300 m².

EXAMPLE 6

De-colorization with Activated Carbon

A total of 77.2 L of solution from SLM process's receiving solution was treated with an activated carbon column of 1 m length, 1.5" column diameter and 0.8 kg carbon.

| | Unit | Before treatment | After treatment |
|---|---|---|---|
| Volume | L | 77.2 | 82.2 |
| Color | Pt-Co | 2000-4000 | 300-500 |

EXAMPLE 7

Deminerization with Strong Cation Exchange Resin

A total of 82.2 L of lactic acid solution that had been treated with activated carbon was treated with a macroporous strong cation exchange resin column of 1 m length, 1.5" diameter and 0.7 kg resin.

| | Unit | Before treatment | After treatment |
|---|---|---|---|
| Volume | L | 82.2 | 84.29 |
| pH | | <1 | <1 |
| Lactate concentration | g/L | 116-121 | 113-118 |
| Sulfate concentration | g/L | <0.8 | <0.8 |
| Ammonium concentration | g/L | <0.8 | Not detectable |
| Color | Pt-Co | 300-500 | 50-100 |

EXAMPLE 8

Removal of Anionic Impurities with Weak Anion Exchange Resin

A total of 84.29 L of deminerized lactic acid solution was treated with a macroporous weak anion exchange resin column of 1 m length, 1.5" diameter and 0.6 kg resin.

| | Unit | Before treatment | After treatment |
|---|---|---|---|
| Volume | L | 84.29 | 86.06 |
| pH | | <2 | <2 |
| Lactate concentration | g/L | 113-118 | 109-114 |
| Sulfate concentration | g/L | <0.8 | Not detectable |
| Ammonium concentration | g/L | Not detectable | Not detectable |

EXAMPLE 9

Product Concentration

88 L of diluted purified lactic acid solution was concentrated to 88% lactic acid concentration.

|  | Unit | Final Product |
| --- | --- | --- |
| pH |  | <1 |
| Lactate concentration | % | 85-90 |
| Sulfate concentration | ppm | <10 |
| Ammonium concentration | ppm | <10 |
| Color | Pt-Co | 0 |
| Glucose concentration | ppm | Not Detectable |

The concentrated broth has the following characteristics:
Effect of Stabilizer in SLM The stability of liquid membrane is highly related to the water transport across the membrane. Higher water transport would result in lower stability. Under the experimental condition, the water transfers from receiving solution to source solution generally. Two new liquid membrane modules constructed with same batch of base polymer fibers were used. The organic layer impregnated in the micropores of the fibers have similar compositions except that one with addition of 0.001-0.02% non-ionic surfactant. The same source of L-lactic acid fermentation broth solution was used for the experiments.

|  | Unit | Without Stabilizer | With Stabilizer |
| --- | --- | --- | --- |
| Lactate extraction flux | g/m2.h | 29 | 24 |
| Extraction time | h | 20 | 20 |
| Initial source solution volume | L | 4 | 4 |
| Final source solution volume | L | 4.2 | 3.9 |
| Total sampling volume | L | ~0.1 | ~0.1 |
| Source solution volume change | L | +0.3 | 0 |
| Number of days stable |  | 7 | More than 180 days |

What is claim is:

1. A process for recovery and purification of lactic acid from a fermentation broth containing lactic acid, the process comprising, in combination, the steps of:
   a. subjecting the fermentation broth to ultralfiltration and/or microfiltration to form a first permeate;
   b. concentrating the first permeate to form concentrated broth;
   c. extracting the lactic acid into a separate stream by passing the concentrated broth through a supported liquid membrane, wherein the supported liquid member comprises a base polymer and an organic layer impregnated on pores of the base polymer, and the organic layer comprises a carrier, a co-extractant, a diluent and a stabilizer;
   d. subjecting the extracted lactic acid solution to activated carbon for removal of colour;
   e. subjecting the extracted lactic acid solution to cation exchange resin for deminerization;
   f. subjecting the extracted lactic acid solution to anion exchange resin for removal of anionic impurities; and
   g. concentrating the extracted lactic acid solution to desired concentration.

2. The process of claim 1, wherein the stabilizer is a form of ethoxylated fluorocarbon based surface-active agent that is non-ionic.

3. The process of claim 2, wherein the stabilizer is selected from a group of ionic, non-ionic detergent or surfactant.

4. The process of claim 1, wherein the carrier is selected from a group consisting of a primary, secondary and tertiary aliphatic and aromatic amine.

5. The process of claim 1, wherein the co-extractant is an aliphatic alcohol.

6. The process of claim 1, wherein the diluent is selected from a group consisting of hydrocarbon, ketone, ether and ester.

7. The process of claim 4, wherein the amine has an alkyl chain of $C_6$ to $C_{24}$.

8. The process of claim 7, wherein the amine has branched, linear or cyclic side chains.

9. The process of claim 5, wherein the aliphatic alcohol has carbon chain Of $C_2$-$C_{29}$.

10. The process of claim 9, wherein the carbon chain can be linear or branched.

11. The process of claim 1, wherein the base polymer is constructed from a group consisting of polypropylene, polyethylene, polyvinyldifluoride, polyethersulfone, polysulfone and polyvinylsulfite.

12. The process of claim 1, wherein the base polymer is constructed from ceramic and metallic materials.

13. The process of claim 1, wherein the supported liquid membrane is of a hollow fiber configuration comprising two sides, one side is of an organic phase and the other side is of an aqueous phase.

14. The process of claim 13, wherein the organic phase contains at least two or more components.

15. The process of claim 1, wherein the ultrafiltration is carried out using ultrafiltration membrane of pore sizes from 0.1 to 0.01 μm.

16. The process of claim 1, wherein the microfiltration is carried out using microfiltration membrane of pore sizes from 0.04 to 1 μm.

17. The process of claim 15 or claim 16, wherein the membrane is constructed from polymeric, metallic or ceramic material.

18. The process of claim 1, wherein the concentrated broth has a pH value of from 1 to 4.8.

19. The process of claim 1, further comprises a step of feeding into the supported liquid membrane in step (c) with water or water mixed with solutes.

20. The process of claim 1, further comprising a step of subjecting the solution obtained from step (f) to activated carbon process.

* * * * *

UNITED STATES PATENT AND TRADEMARK OFFICE
CERTIFICATE OF CORRECTION

PATENT NO. : 8,293,940 B2
APPLICATION NO. : 12/443413
DATED : October 23, 2012
INVENTOR(S) : Ooi Lin Lum, Govindharaju Venkidachalam and Yew Chin Neo It is certified that error appears in the above-identified patent and that said Letters Patent is hereby corrected as shown below:

Column 1, line 26 – Replace "stage." with --stages.--

Column 1, line 46 – Replace "de-mineralized" with --de-mineralize--

Column 1, line 51 – Replace "between of the" with --between the--

Column 2, line 36 – Replace "back extract to" with --back extracted to--

Column 3, line 3 – Replace "the lost of" with --the loss of--

Column 4, line 2 – Replace "comprises two" with --comprising two--

Column 4, line 9 – Replace "to 1" with --to 1 µm.--

Column 6, line 3 – Replace "In situation" with --In a situation--

Column 6, line 18 – Replace "pH; no" with --pH, no--

Column 6, line 37 – Replace "resulting in" with --results in--

Column 7, line 32 – Replace "In generally," with --In general,--

Column 7, line 47 – Replace "phasein" with --phase in--

Column 7, line 53 – Replace "to loss their" with --to lose their--

Column 8, line 2 – Replace "for USG in" with --for use in--

Column 8, line 11 – Replace "resident at" with --reside at--

Signed and Sealed this
Twenty-fifth Day of December, 2012

David J. Kappos
*Director of the United States Patent and Trademark Office*

Column 8, line 11 – Replace "boundary creates" with --boundary created--

Column 8, line 40 – Replace "number ranges" with --number ranging--